(12) United States Patent
Torashima et al.

(10) Patent No.: US 10,371,569 B2
(45) Date of Patent: Aug. 6, 2019

(54) ELECTROSTATIC CAPACITANCE TYPE TRANSDUCER

(71) Applicant: CANON KABUSHIKI KAISHA, Tokyo (JP)

(72) Inventors: Kazutoshi Torashima, Yokohama (JP); Takahiro Akiyama, Atsugi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 141 days.

(21) Appl. No.: 15/519,103

(22) PCT Filed: Oct. 1, 2015

(86) PCT No.: PCT/JP2015/005006
§ 371 (c)(1),
(2) Date: Apr. 13, 2017

(87) PCT Pub. No.: WO2016/059762
PCT Pub. Date: Apr. 21, 2016

(65) Prior Publication Data
US 2017/0219423 A1    Aug. 3, 2017

(30) Foreign Application Priority Data
Oct. 17, 2014    (JP) .................. 2014-212161

(51) Int. Cl.
*G01N 29/24*    (2006.01)
*G01D 5/24*    (2006.01)
(Continued)

(52) U.S. Cl.
CPC ........... *G01H 11/06* (2013.01); *B06B 1/0292* (2013.01); *G01D 5/24* (2013.01); *G01N 29/2406* (2013.01); *G01N 29/2418* (2013.01); *H04R 19/00* (2013.01)

(58) Field of Classification Search
CPC .............. B06B 1/0292; G01N 29/2406; G01N 29/2418; G01H 11/06; G01D 5/24; H04R 19/00
(Continued)

(56) References Cited

U.S. PATENT DOCUMENTS 5,917,264 A * 6/1999 Maruno ................ G01L 9/0073
310/309
6,145,384 A * 11/2000 Ikeda .................... G01D 5/2417
73/780

(Continued)

FOREIGN PATENT DOCUMENTS

EP      1908529 A2    4/2008
JP   2006-352808 A   12/2006
(Continued)

*Primary Examiner* — Jacques M Saint Surin
(74) *Attorney, Agent, or Firm* — Canon U.S.A., Inc. IP Division

(57) ABSTRACT

An electrostatic capacitance type transducer includes one or more elements 2. The one or more elements each include a plurality of cell groups 14 each including a cell 1 including a first electrode 4 and a second electrode 5 arranged with a gap therebetween, the second electrode being electrically connected to a shared signal extraction electrode 15. In the cell group, each of the cells has an equal wiring length from the shared signal extraction electrode 15. The electrostatic capacitance of the plurality of cell groups, the wiring resistance between two adjacent cell groups, the number of cell groups in the element, and the central frequency of the element satisfy a predetermined relationship to increase transmission efficiency or reception sensitivity.

17 Claims, 10 Drawing Sheets

(51) Int. Cl.
  *B06B 1/02* (2006.01)
  *G01H 11/06* (2006.01)
  *H04R 19/00* (2006.01)

(58) Field of Classification Search
  USPC .......................................................... 73/584
  See application file for complete search history.

(56) References Cited

U.S. PATENT DOCUMENTS

| | | |
|---|---|---|
| 9,116,166 B2 * | 8/2015 | Balachandran ......... G01L 25/00 |
| 2009/0313809 A1 | 12/2009 | Kato |
| 2011/0316383 A1 | 12/2011 | Machida |
| 2012/0123268 A1 | 5/2012 | Tanaka |
| 2012/0256518 A1 * | 10/2012 | Torashima ............ B06B 1/0292 |
| | | 310/300 |
| 2012/0256519 A1 | 10/2012 | Tomiyoshi |
| 2014/0010052 A1 | 1/2014 | Torashima |
| 2016/0103100 A1 * | 4/2016 | Akiyama ........... G01N 29/2406 |
| | | 73/628 |
| 2016/0153939 A1 * | 6/2016 | Kato ................. G01N 29/2406 |
| | | 73/606 |

FOREIGN PATENT DOCUMENTS

| | | | |
|---|---|---|---|
| JP | 2008-098697 A | 4/2008 |
| JP | 2008-517736 A | 5/2008 |
| JP | 2011-50098 A | 3/2011 |
| JP | 2012-222514 A | 11/2012 |
| JP | 2014-093510 A | 5/2014 |
| JP | 2014-120874 A | 6/2014 |
| JP | 2014-171695 A | 9/2014 |
| JP | 2014-197197 A | 10/2014 |
| JP | 2015-31942 A | 2/2015 |

* cited by examiner

[Fig. 1A]
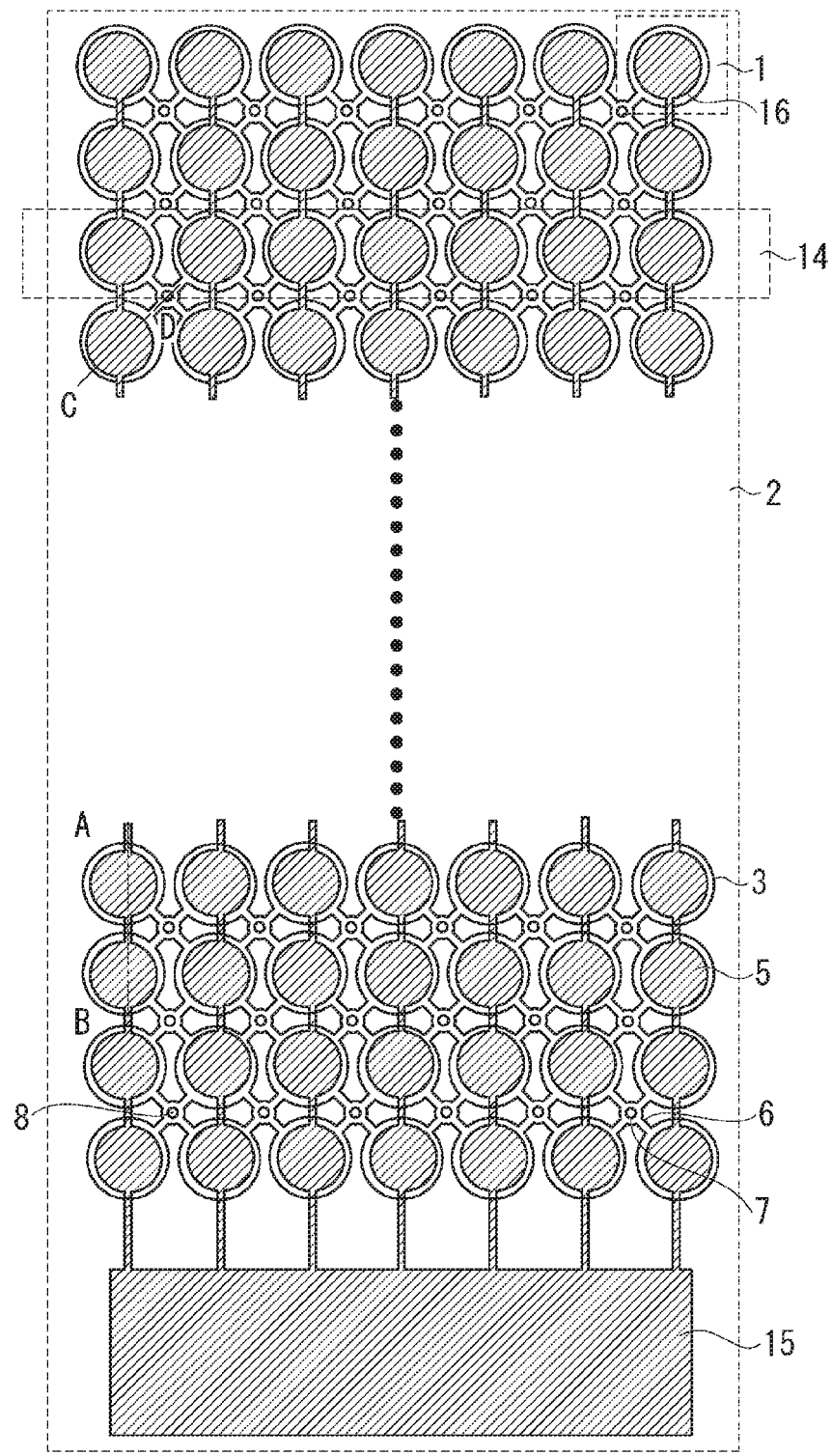

[Fig. 1B]
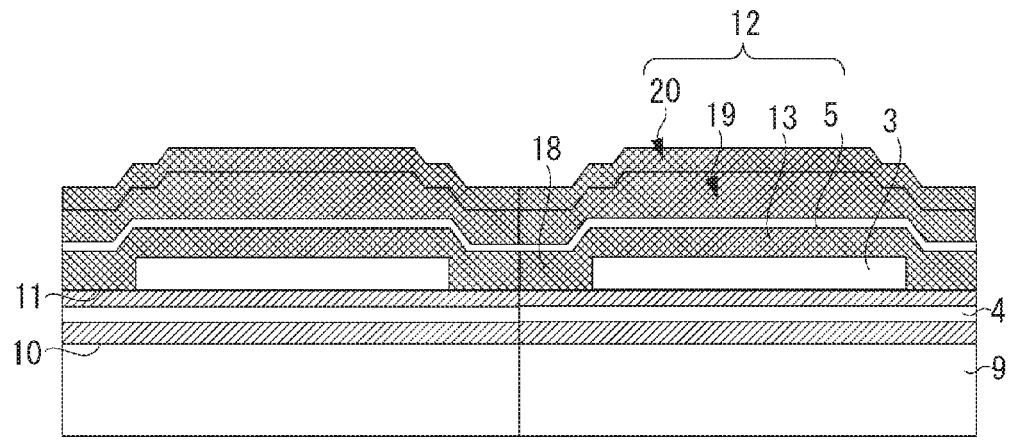
[Fig. 2A]
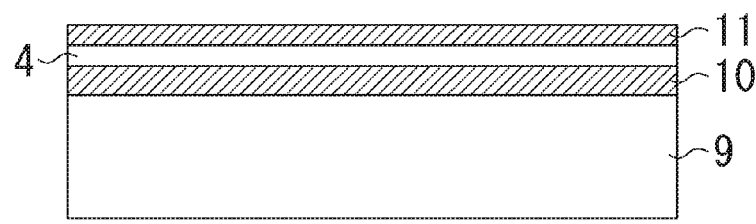
[Fig. 2B]
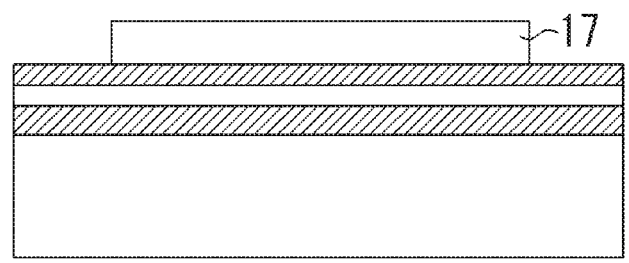
[Fig. 2C]
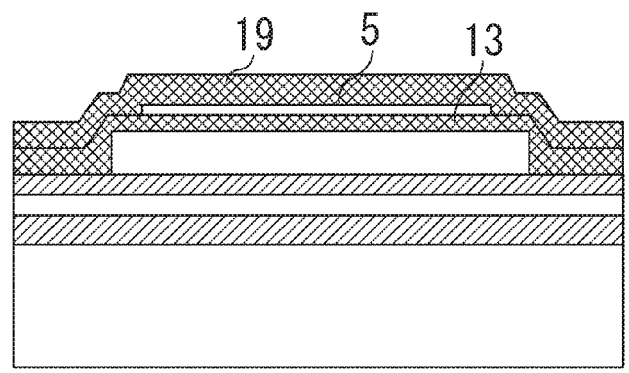

[Fig. 2D]
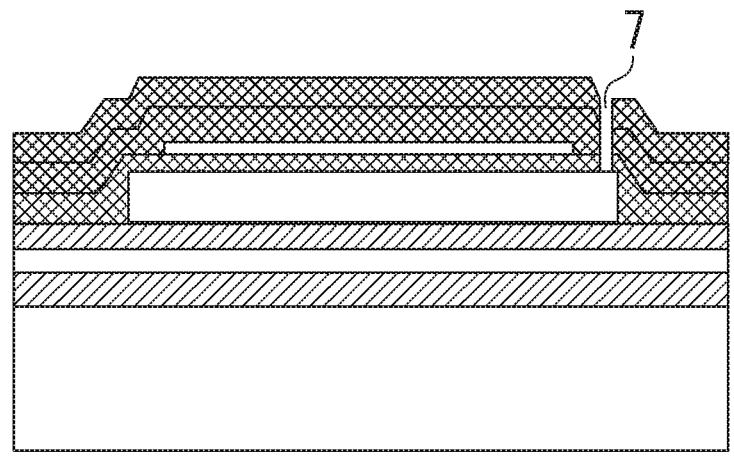
[Fig. 2E]
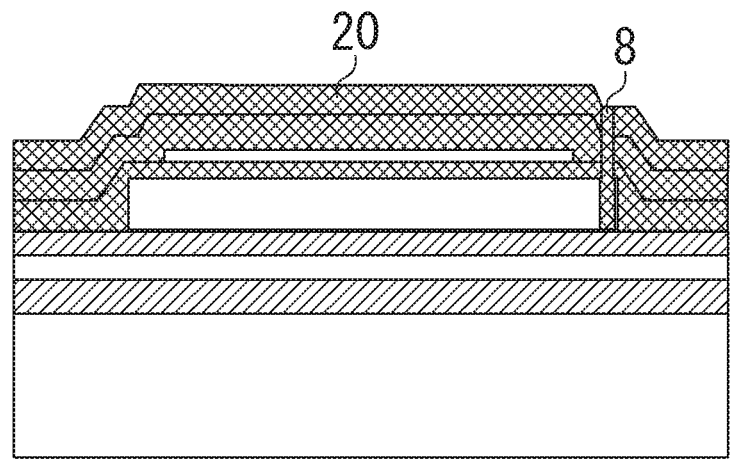

[Fig. 3]
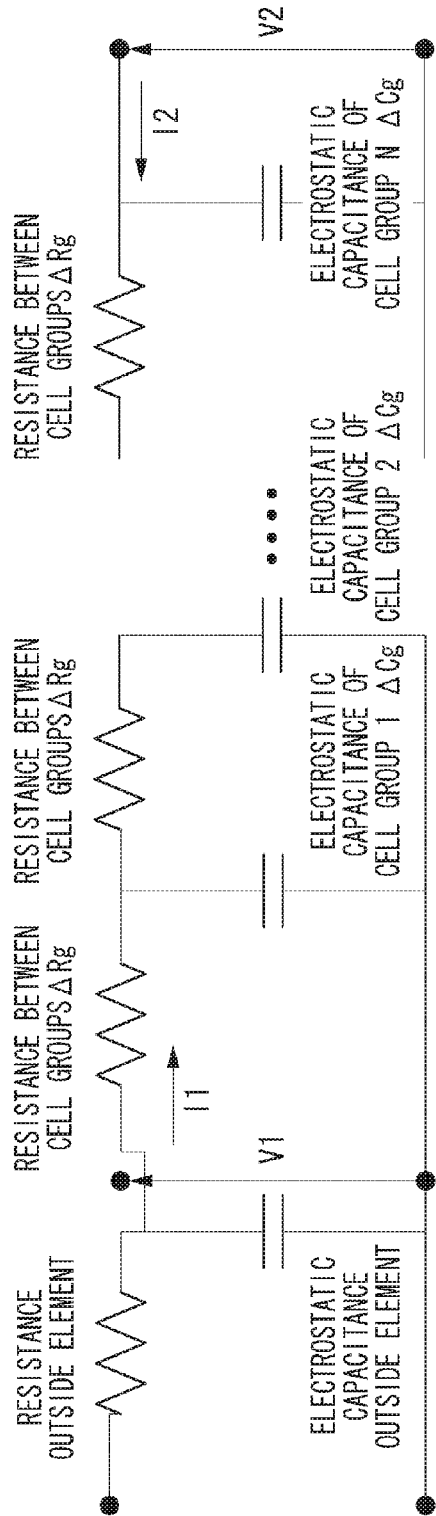

[Fig. 4]
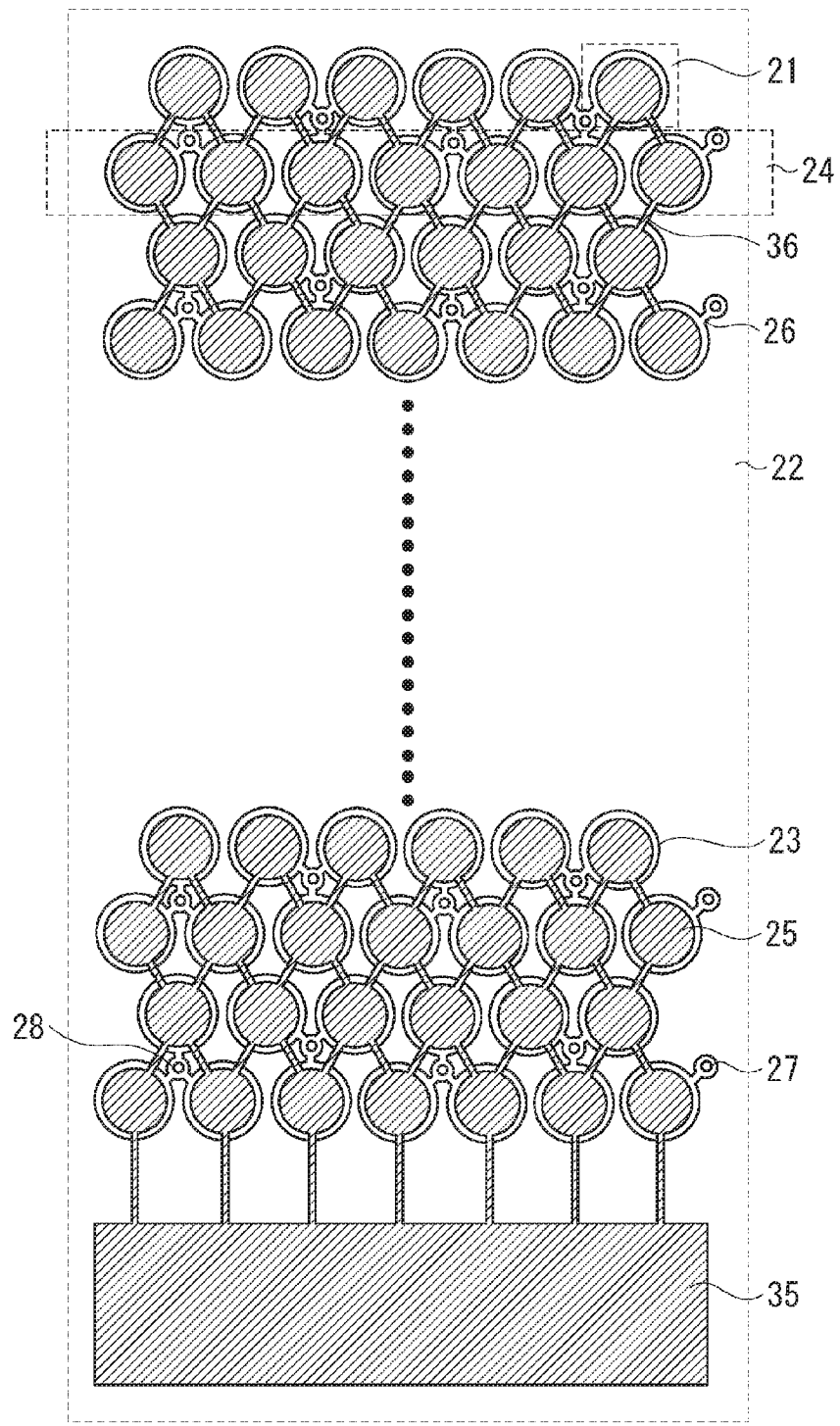

[Fig. 5]
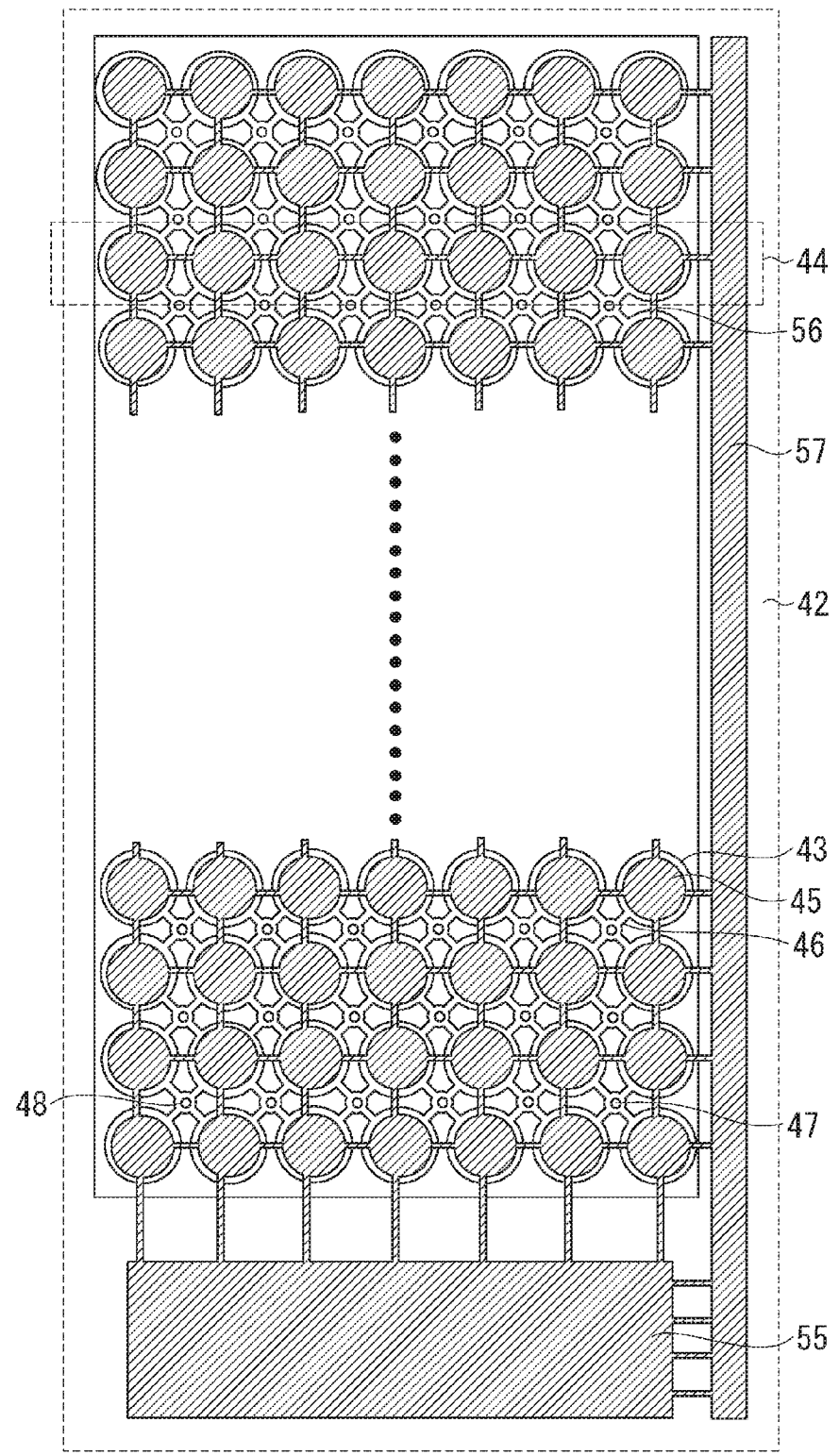

[Fig. 6]
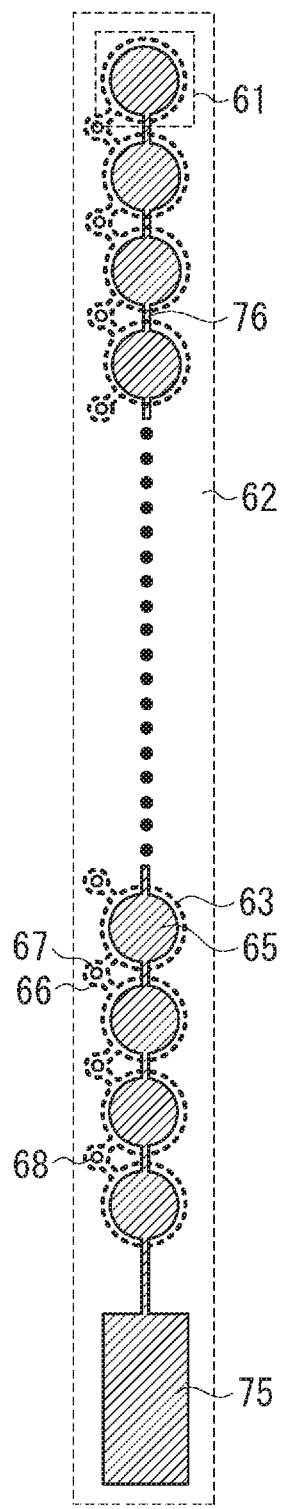

[Fig. 7]
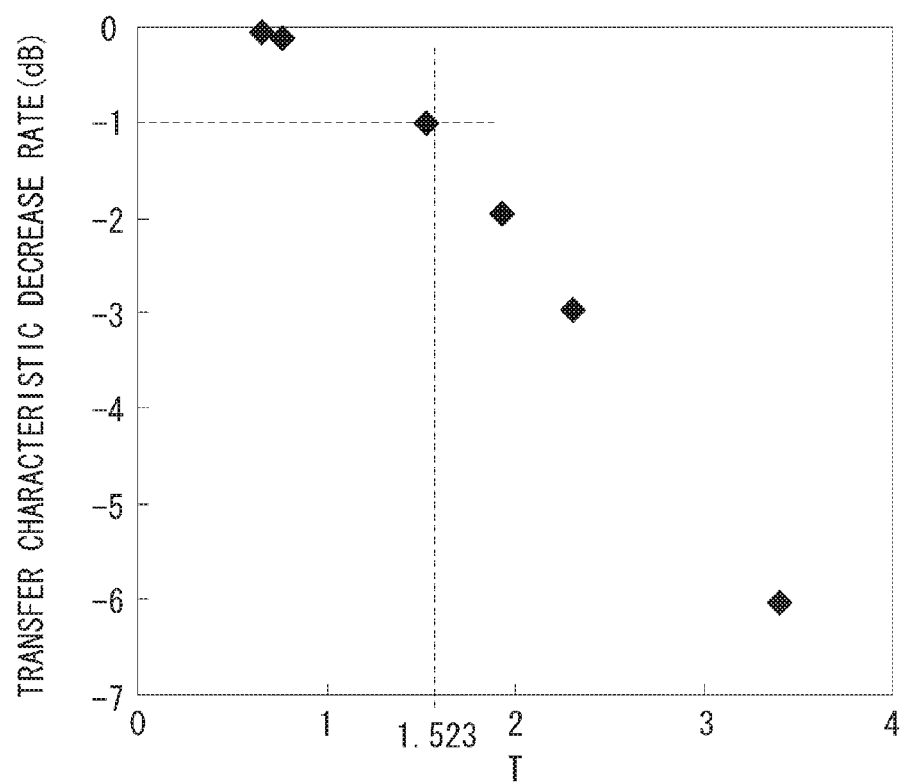

[Fig. 8A]
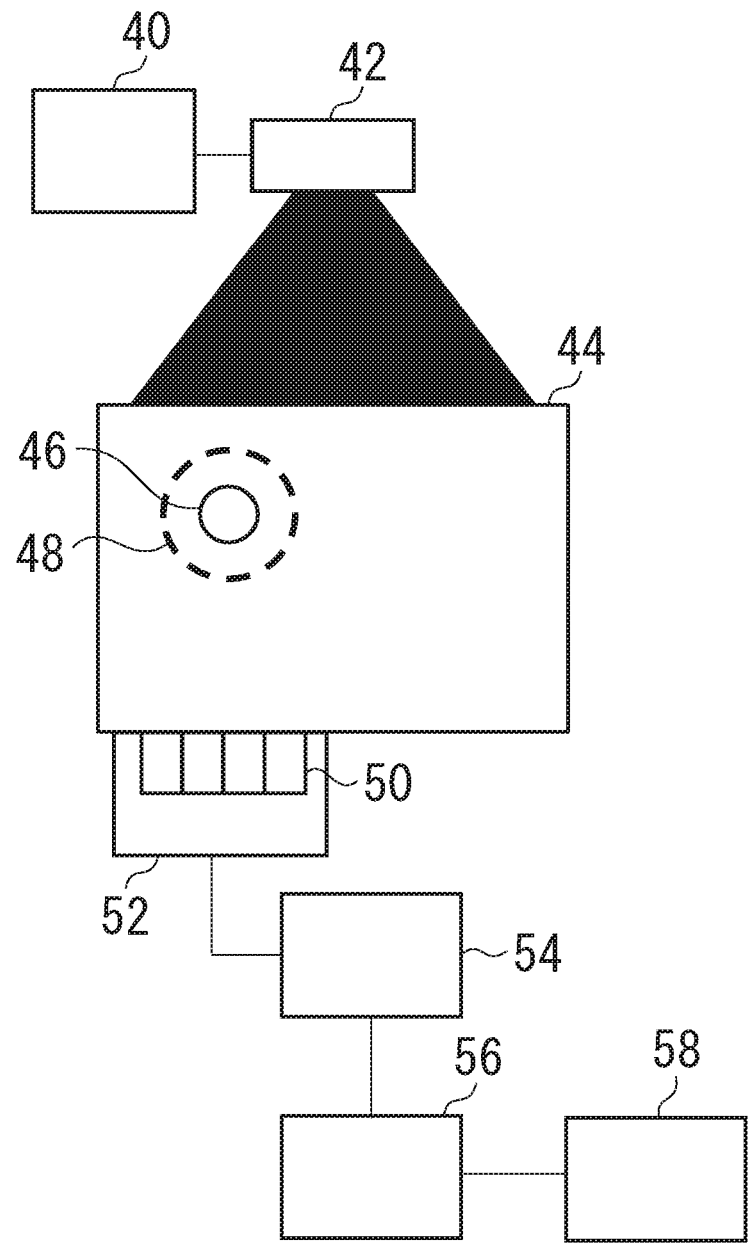

[Fig. 8B]
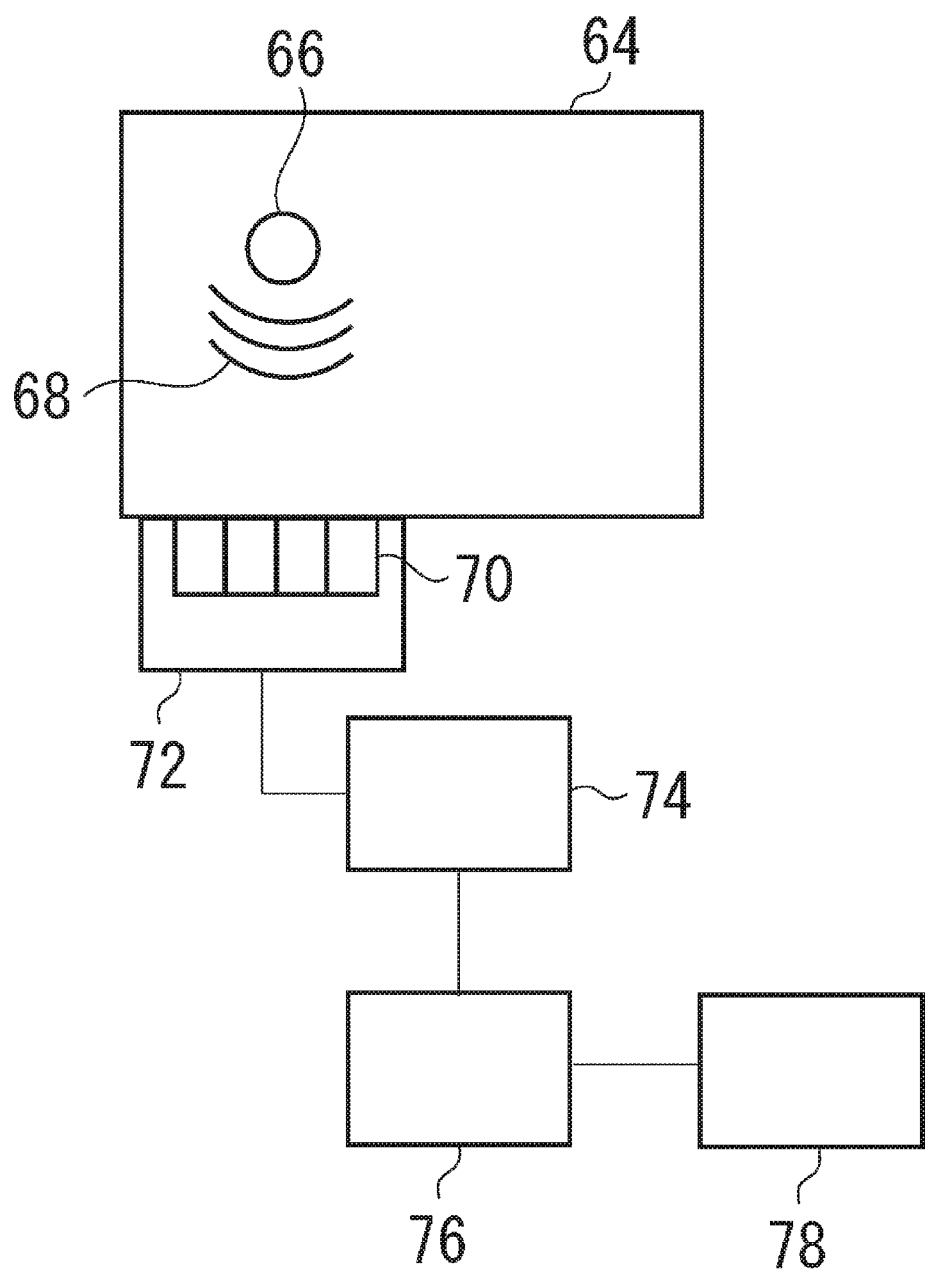

ELECTROSTATIC CAPACITANCE TYPE TRANSDUCER

TECHNICAL FIELD

The present invention relates to an electrostatic capacitance type transducer which is used as an ultrasonic conversion device or the like.

BACKGROUND ART

Conventionally, micromechanical parts manufactured with micromachining technology can be processed at micrometer scale, and various micro-functional devices have been realized using such micromechanical parts. Electrostatic capacitance type transducers using such a technology have been studied as a substitute for a piezoelectric device. Such an electrostatic capacitance type transducer enables transmission and reception of ultrasonic waves by use of vibration of a vibration membrane, and excellent broadband characteristic especially in liquid can be obtained with ease. As such an electrostatic capacitance, an electrostatic capacitance type transducer has been discussed in which a first electrode placed on a substrate and electrical wiring which connects cells with each other are formed using titanium (refer to Patent Literature 1).

CITATION LIST

Patent Literature

PTL 1: Japanese Patent Application Laid-Open No. 2012-222514

SUMMARY OF INVENTION

Technical Problem

In the conventional electrostatic capacitance type transducers described above, in which a first electrode and electrical wiring connecting cells together are formed using titanium, transmission efficiency or reception sensitivity may be decreased.

Solution to Problem

In consideration of the problem discussed above, a first electrostatic capacitance type transducer including one or more elements according to an exemplary embodiment of the present invention has the following feature. The one or more elements each include a plurality of cell groups each including a plurality of cells, the cell including a first electrode and a second electrode arranged with a gap therebetween, the second electrode being electrically connected to a shared signal extraction electrode, and in the cell group, each of the cells has an equal wiring length from the shared signal extraction electrode. The following formula (1)

$$fc \le 1/(2 \times \pi \times Ng^2 \times \Delta Rg \times \Delta Cg) \tag{1}$$

is satisfied, where $\Delta Cg$ is electrostatic capacitance of the cell group, $\Delta Rg$ is wiring resistance between two adjacent cell groups, $Ng$ is the number of cell groups in the element, and $fc$ is a central frequency of the element.

Further, in consideration of the problem discussed above, a second electrostatic capacitance type transducer including one or more cells according to an exemplary embodiment of the present invention has the following feature. The cell includes a first electrode and a second electrode arranged with a gap therebetween, the second electrode being electrically connected to a shared signal extraction electrode, and the one or more cells have a different wiring length from the shared signal extraction electrode. The following formula (2)

$$fc \le 1/(2 \times \pi \times Ns^2 \times \Delta Rs \times \Delta Cs) \tag{2}$$

is satisfied, where $\Delta Cs$ is electrostatic capacitance of the cell, $\Delta Rs$ is wiring resistance between two adjacent cells, $Ns$ is the number of cells, and $fc$ is a central frequency of the electrostatic capacitance transducer.

The structure of the second electrostatic capacitance type transducer can also be regarded as the structure of the first electrostatic capacitance type transducer in which each cell group is constituted by a single cell.

Advantageous Effects of Invention

According to an exemplary embodiment of the present invention, a configuration to satisfy a predetermined relational equation can prevent a decrease in transmission efficiency or reception sensitivity.

Further features of the present invention will become apparent from the following description of exemplary embodiments with reference to the attached drawings.

BRIEF DESCRIPTION OF DRAWINGS

[FIG. 1A] A schematic diagram illustrating an electrostatic capacitance type transducer according to a first exemplary embodiment or Example 1 of the present invention.

[FIG. 1B] A schematic diagram illustrating an electrostatic capacitance type transducer according to a first exemplary embodiment or Example 1 of the present invention.

[FIG. 2A] A cross sectional view illustrating a method for manufacturing the electrostatic capacitance type transducer illustrated in FIG. 1.

[FIG. 2B] A cross sectional view illustrating a method for manufacturing the electrostatic capacitance type transducer illustrated in FIG. 1.

[FIG. 2C] A cross sectional view illustrating a method for manufacturing the electrostatic capacitance type transducer illustrated in FIG. 1.

[FIG. 2D] A cross sectional view illustrating a method for manufacturing the electrostatic capacitance type transducer illustrated in FIG. 1.

[FIG. 2E] A cross sectional view illustrating a method for manufacturing the electrostatic capacitance type transducer illustrated in FIG. 1.

[FIG. 3] A view illustrating a principle according to an exemplary embodiment of the present invention.

[FIG. 4] A top view illustrating an electrostatic capacitance type transducer according to Example 2 of the present invention.

[FIG. 5] A top view illustrating an electrostatic capacitance type transducer according to Example 3 of the present invention.

[FIG. 6] A top view illustrating an electrostatic capacitance type transducer according to Example 4 of the present invention.

[FIG. 7] A view illustrating a transfer characteristic simulation result.

[FIG. 8A] A schematic diagram illustrating an object information acquisition apparatus according to a second exemplary embodiment of the present invention.

[FIG. 8B] A schematic diagram illustrating an object information acquisition apparatus according to the second exemplary embodiment of the present invention.

DESCRIPTION OF EMBODIMENTS

According to an exemplary embodiment of the present invention, an element includes a plurality of cell groups or a plurality of cells and a predetermined relational equation is satisfied to attain an expected purpose. The predetermined relational equation includes the electrostatic capacitance of the cell groups or cells, the wiring resistance between adjacent cell groups or cells, the number of cell groups or cells, and a central frequency of the operation frequency. Various exemplary embodiments and examples of the present invention will be described below but are not intended to limit the scope of the present invention, and various modifications and changes can be made within the spirit of the invention.

First Exemplary Embodiment

A first exemplary embodiment of the present invention is described below. The following describes the first exemplary embodiment of the present invention with reference to the drawings. FIG. 1A is a top view of an electrostatic capacitance type transducer (hereinafter, also referred to as a transducer) according to the present exemplary embodiment, and FIG. 1B is a cross sectional view taken along line A-B in FIG. 1A. Further, FIG. 2 is a cross sectional view taken along line C-D in FIG. 1A and illustrates a method for manufacturing the electrostatic capacitance type transducer according to the present exemplary embodiment.

The electrostatic capacitance type transducer according to the present exemplary embodiment includes one or more electrostatic capacitance type transducer elements 2 (hereinafter, also referred to as an element) having a cell structure (cell) 1. While only one electrostatic capacitance type transducer element 2 is illustrated in FIG. 1A, the number of these elements 2 can be any number. The cell structure 1 includes a substrate 9, a first insulation membrane 10 formed on the substrate 9, a first electrode (lower electrode) 4 formed on the first insulation membrane 10, and a second insulation membrane 11 formed on the first electrode 4. The cell structure 1 further includes a vibration membrane 12, a vibration membrane support member 18 which supports the vibration membrane 12 in such a manner that the vibration membrane 12 can vibrate, and a cavity (space) 3. The vibration membrane 12 includes a first membrane 13, a second electrode (upper electrode) 5, a second membrane 19, and a third membrane 20. In the case where the substrate 9 is an insulating substrate such as a glass substrate, the first insulation membrane 10 can be omitted. The first membrane 13, the second membrane 19, and the third membrane 20 are insulation membranes. As to a material of the membranes, a silicon nitride membrane is desirable because a silicon nitride membrane can be formed at low tensile stress, e.g., 300 MPa or lower, which can prevent large deformation of the vibration membrane due to the residual stress of the silicon nitride membrane.

The plurality of cells 1 constituting the cell group 14 is connected with each other with wiring 16 between the cell groups. The cell group 14 includes a plurality of cells having an equal wiring length from a signal extraction electrode 15 shared in the electrostatic capacitance type transducer element. More specifically, the electrical wiring 16 connects the second electrodes 5 with each other, and connects the cells of adjacent cell groups with each other. In the case where a plane to which the wiring 16 between the cell groups 14 is parallel projected overlaps the first electrode 4, parasitic capacitance occurs. The parasitic capacitance leads to an increase in noise, so that it is desirable the portion where the plane to which the wiring 16 between the cell groups is parallel projected overlaps the first electrode 4 is small. Thus, it is desirable that the width of the wiring between the cell groups is small and that the number of wires in the wiring is small. Furthermore, to make it easy to form a three-dimensional structure such as the cavity 3 on the first electrode 4, it is desirable that the first electrode 4 has a flat surface without asperities. An etching path 6, an etching hole 7, and a sealing member 8 illustrated in FIG. 1 will be described below.

In the electrostatic capacitance type transducer according to the present exemplary embodiment, each of the electrostatic capacitance type transducer elements 2 includes the plurality of cell groups 14 each of which includes the plurality of cells having an equal wiring length from the shared signal extraction electrode 15. That is, each of the elements 2 includes the plurality of cell groups 14. The signal extraction electrode 15 is provided in each of the elements 2. In the present exemplary embodiment, one of a pair of electrodes (second electrode 5 which is a part of the vibration membrane) is electrically insulated between the elements 2, whereas the other one of the pair of electrodes (first electrode 4) is electrically connected between the elements 2. In this arrangement, to prevent a decrease in transmission efficiency or reception sensitivity, electrostatic capacitance $\Delta Cg$ of the cell group 14, electrical resistance $\Delta Rg$ of the wiring 16 between adjacent cell groups 14, the number Ng of cell groups 14, and a central frequency fc of operation frequency of the electrostatic capacitance type transducer satisfy a relationship specified by formula (1). The electrostatic capacitance $\Delta Cg$ includes the electrostatic capacitance of the cell itself and the parasitic capacitance, and the electrical resistance $\Delta Rg$ is the combined resistance of multiple pieces of parallel wiring 16.

$$fc \leq 1/(2 \times \pi \times Ng^2 \times \Delta Rg \times \Delta Cg) \quad (1)$$

The foregoing arrangement prevents a decrease in transmission efficiency or reception sensitivity due to a resistance-capacitance (RC) coupling of the electrostatic capacitance of the cell groups and the electrical resistance between the cell groups. The following describes a decrease in transmission efficiency or reception sensitivity due to the RC coupling. In general, in a case where an electrical resistor R and an electrostatic capacitor C are connected in series, a low-pass filter is formed by the RC coupling. The cutoff frequency of the low-pass filter can be expressed by $1/(2 \times \pi \times R \times C)$. It is known that the electrostatic capacitance or electrical resistance is low in an element in a case of a general electrostatic capacitance type transducer and, since the cutoff frequency by the RC coupling is significantly high, the electrostatic capacitance or electrical resistance is not taken into consideration. When the parasitic resistance outside the element is high, there may be a case where coupling of the parasitic resistance outside the element and the electrostatic capacitance C in the element is taken into consideration. In such a case, the parasitic resistance is decreased to increase the cutoff frequency by the RC coupling.

In the present invention, the problem is found that the transmission efficiency or reception sensitivity decreases due to the RC coupling when the number of cell groups is increased even if the electrostatic capacitance $\Delta C$ of the cell group and the electrical resistance ΔR between the cell groups are small. The transmission efficiency or reception sensitivity decreases due to the RC coupling especially in a case where the number of cells 1 constituting the cell group 14 is small and the number of cell groups 14 is larger than the number of cells 1 constituting the cell group 14 or in a case where the number of cell groups 14 is equal to or larger than 50.

FIG. 3 illustrates a principle according to an exemplary embodiment of the present invention and circuit configuration of the element of the electrostatic capacitance type transducer according to the first exemplary embodiment of the present invention. In the electrostatic capacitance type transducer according to the present exemplary embodiment, the cells having an equal wiring length from the signal extraction electrode 15 can be considered to be electrically equivalent. Thus, these cells are grouped together as a single cell group. As illustrated in FIG. 3, in the case where the number of cell groups 14 is large, the RC coupling by the electrostatic capacitance of the single cell group and the electrical resistance between the cell groups is formed at multiple stages (N stages). In this case, the relationship between V1 and V2 can be expressed as follows. Especially, in the case where the number (N) of cell groups is equal to or larger than 50, a difference between formula (3) and an exact solution is less than 1%.

[Math. 3]

$$\begin{pmatrix} V_1 \\ I_1 \end{pmatrix} = \begin{pmatrix} \cosh(\gamma N) & \sqrt{\Delta R/j\omega \Delta C} \sinh(\gamma N) \\ \frac{1}{\sqrt{\Delta R/j\omega \Delta C}} \sinh(\gamma N) & \cosh(\gamma N) \end{pmatrix} \begin{pmatrix} V_2 \\ I_2 \end{pmatrix} \quad (3)$$

$$\gamma = \sqrt{j\omega \Delta R \Delta C}$$

In formula (3) above, $\sqrt{\Delta R/j\omega \Delta C}$ is Z (impedance). Although Z can be expressed as $Z=\sqrt{(R+j\omega L)/(G+j\omega G)}$, since L (inductance) and G (conductance) are zero, $Z=\sqrt{\Delta R/j\omega \Delta C}$. Further, γ can be expressed as $\sqrt{(R+j\omega L)(G+j\omega C)}$, and, since L and G are zero, $\gamma=\sqrt{j\omega \Delta R \Delta C}$.

In formula (3), since no cell exists outside the cell group farthest from the signal extraction electrode, it can be considered that the impedance is significantly high. Thus, I2 is zero. Accordingly, the relationship between V1 and V2 can be expressed as follows.

$$V1/V2 = \cos h(N\sqrt{(j\omega \Delta R \Delta C)}) \quad \omega = 2\pi f \quad (4)$$

The frequency band of the electrostatic capacitance type transducer is wide, and a decrease in transmission efficiency or reception sensitivity due to the RC coupling can be prevented if V1/V2 in formula (4) above is substantially constant within a frequency band twice as much as a desired central frequency fc. More specifically, V1/V2 is a transfer characteristic (sensitivity), and if V1/V2 does not decrease to about 2fc, a sufficiently high cutoff frequency is obtained, so that a decrease in transmission efficiency or reception sensitivity can be prevented. As used herein, the term "substantially constant" indicates that the transfer characteristic decrease rate is not higher than 1 dB, which is a degree of precision of an apparatus or system for measuring an ultrasonic wave pressure.

From formula (4), if N·(ωΔRΔC), which is a variable, is constant, V1/V2 is constant. FIG. 7 illustrates V1/V2 in dB with $N\sqrt{(\omega \Delta R \Delta C)}$ on the horizontal axis. As illustrated in FIG. 7, from a result of a simulation, it is found that the transfer characteristic decrease rate at 2fc is not higher than 1 dB when $N\sqrt{(\omega \Delta R \Delta C)}$ is equal to or smaller than 1.5. Accordingly, only formula (5) described below needs to be satisfied. That is, 1 (dB)≥cos h(N√(ωΔRΔC)), and formula (5) below can be derived.

$$N\sqrt{(2\pi(2fc)\Delta R \Delta C)} \leq 1.5 \quad (5)$$

Since the square of 1.5 is substantially 2, the above described formula (1) can be derived from formula (5). From the foregoing, if the electrostatic capacitance ΔCg of the cell group, the electrical resistance ΔRg of the wiring 16 between adjacent cell groups, the number Ng of cell groups, and the central frequency fc satisfy the relationship specified by formula (1), V1/V2 becomes substantially constant, so that a decrease in transmission efficiency or reception sensitivity can be prevented.

The following describes a principle of the driving of the transducer. The element of the electrostatic capacitance type transducer can extract an electrical signal from the signal extraction electrode 15. While the second electrode is connected to the extraction electrode to extract an electrical signal in the present exemplary embodiment, an electrical signal can be extracted from the first electrode. In the case of receiving ultrasonic waves by the electrostatic capacitance type transducer, direct-current voltage is applied in advance to the first electrode 4 by a voltage applying unit (not illustrated). When an ultrasonic wave is received, the vibration membrane 12 including the second electrode 5 is deformed. This changes the distance (height) between the second electrode 5 and the first electrode 4 and the electrostatic capacitance changes. The change in the electrostatic capacitance causes electric current to pass through the signal extraction electrode 15. This electric current is converted into voltage by a current-voltage converting element (not illustrated) and then an ultrasonic wave can be received. As described above, the direct-current voltage may be applied to the second electrode 5, and an electrical signal may be extracted from the first electrode 4. On the other hand, direct-current voltage and alternating-current voltage are applied to the second electrode 5, so that the vibration membrane 12 can be vibrated by electrostatic force. As a result, an ultrasonic wave can be transmitted. When the ultrasonic wave is transmitted, the arrangement of the extraction wiring may be changed to apply direct-current voltage and alternating-current voltage to the first electrode 4 so that the vibration membrane is vibrated.

The following describes a manufacturing method according to the present exemplary embodiment with reference to FIGS. 2A, 2B, 2C, 2D, and 2E. FIGS. 2A, 2B, 2C, 2D, and 2E is each a cross sectional view of the electrostatic capacitance type transducer, and the arrangement is substantially the same as that illustrated in FIG. 1, FIG. 2 is a cross sectional view taken along line C-D in FIG. 1. As illustrated in FIG. 2A, the first insulation membrane 10 is formed on the substrate 9. The substrate 9 is a silicon substrate, and the first insulation membrane 10 is formed to create insulation from the first electrode 4. In a case where the substrate 9 is an insulating substrate such as a glass substrate, the insulation membrane 10 does not have to be formed. Furthermore, it is desirable that the substrate 9 is a substrate with small surface roughness. In a case where the surface roughness is large, the surface roughness is also transferred in a subsequent process for forming a membrane and, furthermore, the distance between the first electrode and the second electrode varies among the cells or elements due to the surface roughness. This variation leads to a variation in conversion efficiency and thus to a variation in sensitivity and band.

Accordingly, it is desirable that the substrate 9 is a substrate with small surface roughness.

Next, the first electrode 4 is formed. The first electrode 4 is desirably made of a conductive material with small surface roughness, such as titanium, an aluminum alloy of aluminum and neodymium, etc. As in the case of the substrate, if the surface roughness of the first electrode is large, the distance between the first electrode 4 and the second electrode 5 varies among the cells or elements due to the surface roughness. Accordingly, a conductive material with small surface roughness is desirable. Next, the second insulation membrane 11 is formed. It is desirable that the second insulation membrane 11 is made of an insulating material having small surface roughness. The second insulation membrane 11 is formed to prevent an electrical short circuit or insulation breakdown between the first electrode and the second electrode in the case where voltage is applied between the first electrode 4 and the second electrode 5. In a case where the electrostatic capacitance type transducer is driven at low voltage and a membrane 13 described below is an insulating member, the second insulation membrane 11 does not have to be formed. As in the case of the substrate, if the surface roughness of the second insulation membrane 11 is large, the distance between the first electrode and the second electrode varies among the cells or elements due to the surface roughness. Accordingly, it is desirable that the surface roughness of the second insulation membrane 11 is small. Examples of such a membrane include a silicon nitride membrane, a silicon dioxide membrane, etc.

Next, as illustrated in FIG. 2B, a sacrifice layer 17 is formed. It is desirable that the sacrifice layer 17 is made of a material with small surface roughness. As in the case of the substrate 9, if the surface roughness of the sacrifice layer is large, the distance between the first electrode 4 and the second electrode 5 varies among the cells 1 or elements 2 due to the surface roughness. Accordingly, the surface roughness of the sacrifice layer is desirably small. Furthermore, to shorten the etching time required for removing the sacrifice layer, it is desirable that the sacrifice layer is made of a material that can be etched at high speed. The sacrifice layer 17 should be a material that can substantially prevent the second insulation membrane 11 and the membrane from being etched by an etching solution or etching gas for the removal of the sacrifice layer. In a case where the second insulation membrane 11 and the membrane are comparatively etched by an etching solution or etching gas for the removal of the sacrifice layer, the thickness of the vibration membrane and the distance between the first electrode 4 and the second electrode 5 vary. The variation in the thickness of the vibration membrane and in the distance between the first electrode 4 and the second electrode 5 leads to a variation in sensitivity and band frequency among the cells or elements. In a case where the second insulation membrane 11 and the first membrane 13 are a silicon nitride membrane or a silicon oxide membrane, it is desirable to use chromium, which has small surface roughness and on which an etching solution that does not etch the second insulation membrane and the first membrane is used, as the sacrifice layer material.

Next, as illustrated in FIG. 2C, the first membrane 13, the second electrode 5, and the second membrane 19 are formed. The tensile stresses of the first membrane 13 and the second membrane 19 are desirably low. For example, a tensile stress of 300 MPa or lower is desirable. The tensile stress of a silicon nitride membrane is controllable, and the tensile stress can be controlled to a low tensile stress of 300 MPa or lower. In a case where the first membrane 13 has compression stress, the first membrane may cause sticking (contact with a bottom surface of the cavity) or buckling, which leads to a significant deformation. Furthermore, in a case where the tensile stress is high, the membrane may be damaged. Thus, it is desirable that the tensile stresses of the first membrane 13 and the second membrane 19 are low. It is desirable that the second electrode 5 is made of a material with low residual stress. In a case where the residual stress of the second electrode 5 is high, the high residual stress causes a significant deformation in the vibration membrane 12. Thus, it is desirable that the residual stress of the second electrode is low. Furthermore, in a case where an additional membrane is formed, it is desirable that the second electrode 5 is made of a heat-resistant material. Examples of such materials include titanium, an aluminum alloy, etc. Especially, since an aluminum alloy of aluminum and neodymium has high heat resistance, a change in Properties of the second electrode 5 is prevented, which is caused by the heat at the time of the formation of the second membrane 19 and the third membrane 20.

Next, as illustrated in FIG. 2D, the etching hole 7 is formed. Thereafter, the sacrifice layer 13 is removed through the etching hole 7. Next, as illustrated in FIG. 2E, the sealing member 8 is formed. In this process, the sealing member 8 for sealing the etching hole 7 and the third membrane 20 are formed at the same time. In a case where the process for sealing the etching hole 7 and the process for forming the third membrane 20 are separately carried out, a membrane for sealing the etching hole is accumulated on the vibration membrane 12. If etching is carried out to remove the accumulated membrane, the thickness of the vibration membrane 12 and the stress can vary. In contrast, if sealing the etching hole 7 and forming the third membrane 20 are carried out in the same process as in the present exemplary embodiment, the vibration membrane 12 can be formed only by performing the membrane forming process.

Moreover, the layer including the sealing member 8 is desirably made of a material having low tensile stress. As in the cases of the first membrane 13 and the second membrane 19, if the layer including the sealing member 8 has compression stress, the membrane can cause sticking or buckling, which causes a significant deformation. Furthermore, in a case where the tensile stress is high, the membrane may be damaged. Accordingly, the tensile stress of the third membrane 20 is desirably low. The tensile stress of a silicon nitride membrane is controllable, and the tensile stress can be controlled to a low tensile stress of 300 MPa or lower. Following this process, a process (not illustrated) is performed to form wiring for connecting the first electrode 4, wiring for connecting the second electrode 5, and a signal extraction electrode 15. The wiring material may be aluminum, etc.

In a case where the cavity 3 is formed by removing the sacrifice layer and there is a difference in height among the cells as in the foregoing arrangement, the electrical resistance of the wiring 16 between the cell groups may become high. Especially, in a case where intervals between the cells are small or the difference in height is large, the step coverage is decreased, and the thickness of the electrical wiring may become thin. In the case of the electrostatic capacitance type transducer according to the present exemplary embodiment, the electrostatic capacitance $\Delta Cg$ of the cell group, the electrical resistance $\Delta Rg$ of the wiring 16 between adjacent cell groups, the number Ng of cell groups, and the central frequency fc satisfy the relationship specified in formula (1), so that a decrease in transmission efficiency or reception sensitivity can be prevented.

The electrical wiring for connecting the second electrodes of the plurality of cells may be disposed only between adjacent cell groups, and the electrical wiring connects the electrodes of all the nearest neighboring cells (refer to Example 2 described below). Such an arrangement can prevent an increase in unnecessary parasitic capacitance, which leads to an increase in noise, so that the electrical resistance between the cell groups can be decreased.

Furthermore, the electrical wiring between the cell groups may be made of an alloy of aluminum and neodymium. In the case where the second membrane 19 is formed after the second electrode 5 is formed as illustrated in FIG. 2, fine bumps called hillocks may be formed in a metal such as aluminum by heat, which is generated at the time of the formation, and may cut through and break the vibration membrane. Use of the material of the foregoing arrangement in the second electrode 5 prevents the occurrence of hillocks and breakage in the vibration membrane 12.

Moreover, the electrostatic capacitance type transducer may include a plurality of cells having different wiring lengths from the signal extraction electrode 15 (refer to Example 4 described below). In such a case, to prevent a decrease in transmission efficiency or reception sensitivity, the electrostatic capacitance $\Delta Cs$ of the cell, the wiring resistance $\Delta Rs$ between adjacent cells, the number Ns of cells having different wiring lengths, and the central frequency fc satisfy the relationship specified in formula (2) above.

Furthermore, the electrostatic capacitance type transducer may include bypass wiring connecting the signal extraction electrode 15 with the second electrode 5. A plane to which the bypass wiring is parallel projected does not overlap the first electrode (refer to Example 3 described below). This arrangement can prevent an increase in the parasitic capacitance, which leads to an increase in noise, so that the electrical resistance between the cell groups can be decreased.

Second Exemplary Embodiment

A second exemplary embodiment of the present invention is described below. The electrostatic capacitance type transducer described in the foregoing exemplary embodiment can be applied to an object information acquisition apparatus that uses acoustic waves. In the object information acquisition apparatus, the electrostatic capacitance type transducer receives acoustic waves from an object and outputs an electrical signal. The output electrical signal is used to acquire object information reflecting optical characteristic values of the object such as an optical absorption coefficient and object information reflecting a difference in acoustic impedance.

FIG. 8A illustrates an object information acquisition apparatus that uses photo-acoustic effect. A light source 40 irradiates an object 44 with pulse light, which is generated by the light source 40, via an optical member 42 such as a lens, a mirror, an optical fiber, etc. An optical absorption member 46 within the object 44 absorbs energy of the pulse light and generates a photo-acoustic wave 48, which is an acoustic wave. A transducer 50 in a probe 52 receives the photo-acoustic wave 48, converts the received photo-acoustic wave 48 into an electrical signal, and outputs the converted electrical signal to a signal processing unit 54. The signal processing unit 54 performs signal processing such as analog/digital (A/D) conversion, amplification, etc. on the input electrical signal and outputs the electrical signal to a data processing unit 56. The data processing unit 56 uses the input signal to acquire object information (characteristic information reflecting optical characteristic values of the object such as an optical absorption coefficient) as image data. Here, the signal processing unit 54 and the data processing unit 56 are collectively referred to as a processing unit. A display unit 58 displays an image based on the image data input from the data processing unit 56.

FIG. 8B illustrates an object information acquisition apparatus that uses the reflection of acoustic waves, such as an ultrasonic echo diagnostic apparatus, etc. An acoustic wave transmitted from a transducer 70 in a probe 72 to an object 64 is reflected by a reflecting member 66. The transducer 70 receives the reflected acoustic wave 68 (reflected wave), converts the reflected acoustic wave 68 into an electrical signal, and outputs the electrical signal to a signal processing unit 74. The signal processing unit 74 performs signal processing such as A/D conversion and amplification on the input electrical signal and outputs the electrical signal to a data processing unit 76. The data processing unit 76 (acquisition unit) uses the input signal to acquire object information (characteristic information reflecting a difference in acoustic impedance) as image data. Here, the signal processing unit 74 and the data processing unit 76 are collectively referred to as a processing unit. A display unit 78 displays an image based on the image data input from the data processing unit 76.

The probe may be a mechanically-scanning probe or a probe (hand-held probe) to be moved by a user such as a doctor or engineer with respect to an object. Further, in the case of an apparatus using reflected waves as illustrated in FIG. 8B, a probe for transmitting acoustic waves may be provided separately from a probe for receiving the acoustic waves.

Furthermore, the object information acquisition apparatus may include the functions of both of the apparatuses illustrated in FIGS. 8A and 8B and acquire both the object information reflecting the optical characteristic values of the object and the object information reflecting the difference in acoustic impedance. In this case, the transducer 50 in FIG. 8A may be configured to perform not only the reception of photo-acoustic waves but also the transmission of acoustic waves and the reception of reflected waves.

The following describes the present invention in detail with reference to more specific examples.

Example 1

The following describes Example 1 of the present invention with reference to FIG. 1. FIG. 1A is a top view of an electrostatic capacitance type transducer according to Example 1, and FIG. 1B is a cross sectional view taken along line A-B in FIG. 1A. The electrostatic capacitance type transducer according to Example 1 includes an electrostatic capacitance type transducer element 2 inducting a cell structure 1. While one electrostatic capacitance type transducer element 2 is illustrated in FIG. 1, the number of electrostatic capacitance type transducer elements 2 may be any number. Further, the electrostatic capacitance type transducer element 2 includes 868 cell structures. While the vibration membrane according to Example 1 is in the shape of a circle, the shape of the vibration membrane may be quadrangular, hexagonal, etc.

The cell structure 1 includes a silicon substrate 9 having a thickness of 300 μm, a first insulation membrane 10 formed on the silicon substrate 9, a first electrode 4 formed on the first insulation membrane 10, and a second insulation membrane 11 formed on the first electrode 4. The cell structure 1 further includes a vibration membrane 12, a vibration membrane support member 18 supporting the vibration membrane 12, and a cavity 3. The vibration membrane 12 includes a first membrane 13, a second membrane 19, a second electrode 5, and a third membrane 20. The first insulation membrane 10 is a silicon oxide membrane formed by thermal oxidation and having a thickness of 1 μm. The second insulation membrane 11 is a silicon oxide membrane formed by plasma-enhanced chemical vapor deposition (PE-CVD). The first electrode 4 is titanium having a thickness of 50 nm, and the second electrode 5 is an alloy of aluminum and neodymium and has a thickness of 100 nm. The first membrane 13 and the second membrane 19 are silicon nitride membranes formed by PE-CVD and are formed at a tensile stress of 200 MPa or lower.

Further, the diameter of the cavity is 30 μm. The thicknesses of the first membrane, the second membrane, and the third membrane are 0.4 μm, 0.5 μm, and 0.7 μm, respectively. The diameter of the first electrode 4 is 26 μm. The depth of the cavity is 0.2 μm. Further, the electrostatic capacitance type transducer element 2 includes 124 cell groups 14 each including seven cells having an equal wiring length from the signal extraction electrode. The electrostatic capacitance $\Delta Cg$ of the cell groups is set to 0.2 pF. The electrical resistance $\Delta Rg$ of the wiring 16 between adjacent cell groups is set to 6Ω. The number Ng of cell groups is set to 124. The central frequency fc is set to 8 MHz. In this way, the relationship specified in formula (1) is satisfied. This arrangement can prevent a decrease in transmission efficiency or reception sensitivity.

Further, the second membrane is formed after the second electrode is formed. Since the alloy of aluminum and neodymium is used as the second electrode, formation of fine bumps called hillocks due to heat, which is generated at the time of the formation of the second membrane, can be prevented. Consequently, breakage in the vibration membrane is prevented.

Example 2

The following describes the structure of an electrostatic capacitance type transducer according to Example 2 with reference to FIG. 4. FIG. 4 is a top view of the electrostatic capacitance type transducer according to Example 2. The structure of the electrostatic capacitance type transducer according to Example 2 is substantially the same as that in Example 1.

According to Example 2, electrical wiring 36 connecting second electrodes 25 of a plurality of cells 21 of an electrostatic capacitance type transducer element 22 is disposed only between adjacent cell groups 24. The electrical wiring connecting the second electrodes 25 of the plurality of cells 21 connects the electrodes of all the nearest neighboring cells with each other. Since there is no electrical wiring connecting the cells 21 of the same cell group 24, an increase in the parasitic capacitance, which causes an increase in noise, can be prevented.

Furthermore, the cell groups 24 are connected with each other by two pieces of electrical wiring with respect to one cell so that the electrical resistance between the cell groups can be decreased. This arrangement can prevent a decrease in transmission efficiency or reception sensitivity. In FIG. 4, a cavity 23, an etching path 26, an etching hole 27, a sealing n ember 28, and a signal extraction electrode 35 are illustrated.

Example 3

The following describes a structure of an electrostatic capacitance type transducer according to Example 3 with reference to FIG. 5. FIG. 5 is a top view of the electrostatic capacitance type transducer according to Example 3. The structure of the electrostatic capacitance type transducer according to Example 3 is substantially the same as that in Example 1.

The electrostatic capacitance type transducer according to Example 3 includes bypass wiring 57 connecting a signal extraction electrode 55 with a second electrodes 45, and a plane to which the bypass wiring 57 is parallel projected does not overlap a first electrode. This arrangement can prevent an increase in the parasitic capacitance which leads to an increase in noise, so that the electrical resistance between the cell groups 44 can be decreased significantly. Thus, the arrangement can prevent a decrease in transmission efficiency or reception sensitivity. In FIG. 5, an electrostatic capacitance type transducer element 42, a cavity 43, an etching path 46, an etching hole 47, a sealing member 48, and wiring 56 between the cell groups are illustrated.

Example 4

The following describes a structure of an electrostatic capacitance type transducer according to Example 4 with reference to FIG. 6. FIG. 6 is a top view of the electrostatic capacitance type transducer according to Example 4. The structure of the electrostatic capacitance type transducer according to Example 4 is substantially the same as that in Example 1.

The electrostatic capacitance type transducer according to Example 4 includes 124 steps of cells 61 (cell group includes a single cell) having a different wiring length from a signal extraction electrode 75. The electrostatic capacitance $\Delta Cs$ of the cell 61 is set to 0.03 pF. The electrical resistance $\Delta Rs$ of wiring 76 between adjacent cells is set to 36Ω. The number Ng of cells is set to 124. The central frequency fc is set to 8 MHz. In this way, the relationship specified in formula (2) is satisfied.

$$fc \leq 1/(2 \times \pi \times Ns^2 \times \Delta Rs \times \Delta Cs) \tag{2}$$

The arrangement according to Example 4 can prevent a decrease in transmission efficiency or reception sensitivity, same as those described above. In FIG. 6, an electrostatic capacitance type transducer element 62, a cavity 63, a second electrode 65, an etching path 66, an etching hole 67, and a sealing member 68 are illustrated.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-212161, filed Oct. 17, 2014, which is hereby incorporated by reference herein in its entirety.

REFERENCE SIGNS LIST

1 Cell structure (cell)
2 Element
3 Cavity (space)
4 First electrode (the other one of the electrodes)
5 Second electrode (one of the electrodes)
14 Cell group
15 Signal extraction electrode
16 Wiring between cell groups

The invention claimed is:

1. An electrostatic capacitance type transducer having an operational central frequency fc, comprising:
   one or more elements each of which includes N cell groups and a signal extraction electrode that is shared among the N cell groups,
   wherein each of the N cell groups includes P cells,
      wherein each of the P cells includes a first electrode and a second electrode arranged with a gap therebetween,
      wherein the second electrode is electrically connected to the signal extraction electrode,
   wherein, in each of the N cell groups, each of the P cells has an equal wiring length from the signal extraction electrode, and
   wherein $fc \leq 1/(2 \times \pi \times N^2 \times \Delta Rg \times \Delta Cg)$, where $\Delta Cg$ is electrostatic capacitance of each of the N cell groups, $\Delta Rg$ is wiring resistance between two adjacent cell groups in the N cell groups.

2. The electrostatic capacitance type transducer according to claim 1, comprising the elements and the signal extraction electrode,
   wherein the second electrode is electrically insulated between the elements.

3. The electrostatic capacitance type transducer according to claim 2, wherein the first electrode is electrically connected between the elements.

4. The electrostatic capacitance type transducer according to claim 1, wherein the cell includes a vibration membrane which is supported so as to be able to vibrate, and
   wherein the second electrode is a part of the vibration membrane which is supported so as to be able to vibrate.

5. The electrostatic capacitance type transducer according to claim 4, wherein the second electrode is an alloy of aluminum and neodymium.

6. The electrostatic capacitance type transducer according to claim 1, wherein the element includes electrical wiring connecting the second electrodes with each other, and
   wherein the electrical wiring connects the cells of different adjacent cell groups with each other and does not connect the cells of the same cell group.

7. The electrostatic capacitance type transducer according to claim 6, wherein the plurality of cell groups includes a first cell group and a second cell group which are adjacent each other, and
   wherein the electrical wiring connects one cell in the first cell group to a plurality of cells in the second cell group.

8. The electrostatic capacitance type transducer according to claim 6, wherein the electrical wiring is an alloy of aluminum and neodymium.

9. The electrostatic capacitance type transducer according to claim 1, wherein the first electrode is an alloy of aluminum and neodymium.

10. The electrostatic capacitance type transducer according to claim 1, further comprising bypass wiring that connects the signal extraction electrode to the second electrode in each of the N cell groups, and
    wherein a plane to which the bypass wiring is projected does not overlap the first electrode.

11. An electrostatic capacitance type transducer having an operational central frequency fc, comprising P cells,
    wherein each of the P cells includes a first electrode and a second electrode arranged with a gap therebetween,
    wherein the second electrode is electrically connected to a signal extraction electrode that is shared among the P cells,
    wherein the P cells have different wiring lengths from the signal extraction electrode, and
    wherein $fc \leq 1/(2 \times \pi \times P^2 \times \Delta Rs \times \Delta Cs)$ is satisfied, where $\Delta Cs$ is electrostatic capacitance of each of the P cells, $\Delta Rs$ is wiring resistance between two adjacent cells in the P cells.

12. An information acquisition apparatus comprising:
    an electrostatic capacitance type transducer configured to receive an acoustic wave from an object and convert the acoustic wave into an electrical signal; and
    an acquisition unit configured to acquire information about the object by use of the electrical signal,
    wherein the electrostatic capacitance type transducer is the electrostatic capacitance type transducer according to claim 1.

13. The information acquisition apparatus according to claim 12, wherein the electrostatic capacitance type transducer transmits an acoustic wave to the object and receives the acoustic wave reflected by the object.

14. The information acquisition apparatus according to claim 12, wherein the electrostatic capacitance type transducer receives an acoustic wave generated by irradiation of the object with light.

15. The information acquisition apparatus according to claim 14, further comprising a light source configured to irradiate the object with light.

16. An electrostatic capacitance type transducer having an operational central frequency, comprising:
    one or more elements each of which includes N cell groups and a signal extraction electrode that is shared among the N cell groups,
    wherein each of the N cell groups includes P cells,
       wherein each of the P cells includes a first electrode and a second electrode arranged with a gap therebetween,
       wherein the second electrode is electrically connected to the signal extraction electrode,
    wherein N and P are positive integers,
    wherein, in each of the N cell groups, each of the P cells has an equal wiring length from the signal extraction electrode, and
    wherein the operational central frequency is less than or equal to an expression scaled by N.

17. An electrostatic capacitance type transducer having an operational central frequency, comprising P cells,
    wherein each of the P cells includes a first electrode and a second electrode arranged with a gap therebetween,
    wherein P is a positive integer,
    wherein the second electrode is electrically connected to a signal extraction electrode,
    wherein the P cells have different wiring lengths from the signal extraction electrode, and
    wherein the operational central frequency is less than or equal to an expression scaled by P.

* * * * *